United States Patent [19]

Trias

[11] 4,286,469

[45] Sep. 1, 1981

[54] OPTICAL FIBER TEST APPARATUS

[75] Inventor: John A. Trias, La Mesa, Calif.

[73] Assignee: The United States of America as represented by the Secretary of the Navy, Washington, D.C.

[21] Appl. No.: 119,058

[22] Filed: Feb. 6, 1980

[51] Int. Cl.³ .............................................. G01N 3/08
[52] U.S. Cl. .................................................... 73/829
[58] Field of Search ................... 73/829, 828, 830, 826

[56] References Cited

U.S. PATENT DOCUMENTS

| 1,987,787 | 1/1935 | Miller | 73/829 |
|---|---|---|---|
| 3,285,052 | 11/1966 | Lothrop | 73/830 |
| 3,643,497 | 2/1972 | LeCompte | 73/829 |
| 3,881,346 | 5/1975 | Scheucher | 73/829 |

*Primary Examiner*—Anthony V. Ciarlante

*Attorney, Agent, or Firm*—Richard S. Sciascia; Ervin F. Johnston; Thomas Glenn Keough

[57] ABSTRACT

Fibers, particularly optical fibers, are tested for determining their tensile strength in expected environments. A pair of sheaves, on journaled and the other fixed receive a looped length of fiber and are placed within a cylindrical shell which is filled with an expected environmental medium, such as seawater. The sheaves are pulled apart subjecting the fiber to tensile loading and a strain gauge provides responsive read-outs so that the fiber's fatigue strength can be determined. The size of the sheaves and adhesively securing the loose ends of the fiber prevents the generation of any spurious pinching torsional stresses. Placing the fiber in the environmental fluid allows a monitoring of the effects of the fluid on the fiber's cladding and core so that the strength limits of the fiber are accurately determined under simulated operational conditions.

5 Claims, 1 Drawing Figure

U.S. Patent    Sep. 1, 1981    4,286,469
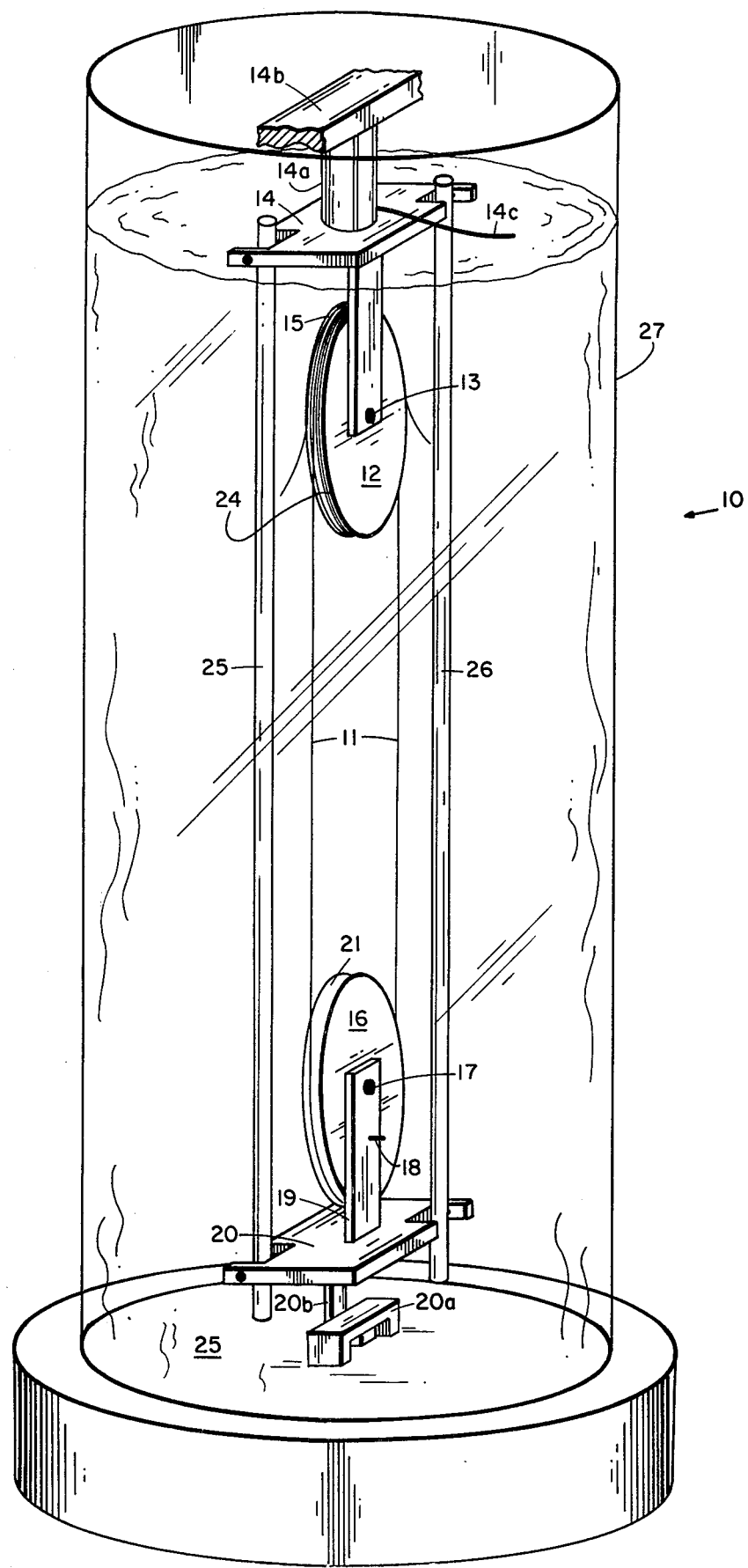

OPTICAL FIBER TEST APPARATUS

BACKGROUND OF THE INVENTION

A wide variety of small fibers such as those used for making clothing and other woven and knit materials frequently are not tested for their tensile strength. Generally speaking, this is not such a critical parameter since usually there is such a multitude of fibers that they additively provide sufficient strength.

Other similarly dimensioned small fibers that are attracting a great detail of attention are the optical fibers. These may be only a few microns in diameter and serve to transmit vast amounts of data by optical means to expedite communications, data processing, etc. Just recently however, designers have begun to appreciate not only the data transfer capability but the considerable inherent tensile strength of these fibers so that they function not only as the information path but also as the strength member between a pair of stations.

These capabilities have not escaped the attention of marine scientists who wish to transfer information to and from undersea instrumentation packages. In addition to the huge data transfer capability and strength, the fibers have lower power requirements and are not influenced by external electromagnetic energy as are relatively heavier contemporary metallic conductors. Furthermore, the optical fibers are capable of transmitting certain types of data with less distortion as compared to the metallic conductors.

Because the fibers were intended to extend for several kilometers in certain instances, the exact limits of the fibers' strengths had to be determined. The hostile ocean environment with its currents, surge and wave action demands fibers that could withstand these continuing abuses. It became imperative that the fibers' strengths be known so that suitable modification, e.g. sufficient numbers of fibers, could be incorporated to provide a reliable data length.

Testing of individual ones of the fibers was difficult because with all of the known tensile load analyzers the fiber was clamped before the tensile forces were applied. Usually where this clamping occurred, additional spurious stresses were created which contributed to a premature failure. Wrapping the fibers about rods or tying them tended to create failure inducing torsional stresses. Either way, the pinching stresses or torsional stresses affected the actual value of the fiber's fatigue strength. Thus, there is a continuing need in the state-of-the-art for a fiber optic test apparatus that does not create failure inducing stresses so as to provide accurate indications of fiber strength.

SUMMARY OF THE INVENTION

The present invention is directed to providing an apparatus for mounting a fiber to allow a strain gauge's determination of the fiber's tensile strength in a variety of environments. A rotatable rounded bearing surface being shaped to receive a fiber is journaled in a fixed support and has a radius of curvature greatly in excess of the fiber's diameter. A similarly configured fixed rounded bearing surface is connected to the strain gauge and has an adhesively mounting means disposed thereon to receive a wrapped length of the fiber to secure it thereon without generating the failure inducing stresses.

It is a prime object of the invention to provide an apparatus for reliably testing fibers.

It is another object of the invention to provide an apparatus which does not generate spurious failure inducing stresses.

Another object is to provide an apparatus having a pair of sheaves receiving a fiber, the sheaves having a diameter greatly in excess of the fiber's diameter to avoid the generation of torsional stresses.

Yet another object is to provide a fiber test apparatus capable of being immersed along with a fiber in a variety of expected environments.

Still another object is to provide an apparatus for testing fibers which employs an adhesive strip mounted on a sheave for securing the fiber to avoid the generation of the spurious stresses otherwise attributed to clamps or pinching devices.

These and other objects of the invention will become more readily apparent from the ensuing specification and claims when taken with the accompanying drawings.

BRIEF DESCRIPTION OF THE DRAWING

The drawing depicts an isometric example of an illustrative embodiment of the invention.

DESCRIPTION OF THE PREFERRED EMBODIMENT

Referring now to the drawing, the optical fiber test apparatus 10 has an optical fiber 11 undergoing a tensile load test in a simulated operational environment. By its unique configuration, such a test is routinely performed in the laboratory and closely approximates the loading of a fiber in, for example, seawater.

The test apparatus is shaped to accommodate any one of several commercially availble tensile load analyzers. One that has worked quite well is the Model 1122 manufactured by the Instron Corporation of Canton, Massachusetts. This analyzer is capable of creating precisely regulated loads and provides a visual indication of the magnitude of the forces exerted across a test fiber.

The test apparatus includes a rotatable sheave 12 journaled on a shaft 13 which, in turn, is rigidly attached to a projection from a crosshead 14.

A strain gauge 14a interconnects the crosshead to the support to a frame member 14b of the tensile load analyzer. A lead 14c reaches from the strain gauge to the analyzer's instrumentation to present responsive readouts.

The periphery of the sheave is provided with an annular groove 15 for receiving the fiber. It is to be noted that the diameter of the sheave is much, much greater, about ten centimeters, when compared to the diameter of the fiber, a few microns. This is to avoid the creation of any spurious tortional stresses which might otherwise occur if a fiber were wrapped about a peg-sized projection or inserted through a hole and subjected to a tensile load.

A similarly configured fixed sheave 16 is mounted on a shaft 17 but a pin 18 also extends through the fixed sheave. The pin secures the sheave onto a support member 19 and crosshead 20 to prevent any rotational motion. Like the rotatable sheave, the fixed sheave is provided with an annular groove about its periphery to receive a test fiber and has a diameter greatly in excess of the diameter of the fiber. A loop-shaped member 20a extends from the crosshead and serves to releaseably connect the fixed sheave to a hook-shaped portion 20b on base portion 25 of the tensile load analyzer. The purpose of such an interconnection is to attach the fiber specimen holder for ease of loading and unloading many fiber specimens for a statistical fatigue strength analysis.

A length of an adhesive double-stick tape 24 is provided through the length of the annular groove of the rotatable sheave. The tape secures the fiber in place during a test operation and avoids creating any spurious "pinching" stresses since clamps, clasps, and related pinching fastners have been found to cause weakening in some fibers. Obviously, erroneous readings result from premature failure.

A pair of rods 25 and 26 extend between the two crossheads and are releaseably secured to the crossheads by any one of a variety of ways such as by pinning, bolting, clamping, etc. The rods serve to couple the two sheaves together and to maintain a spaced relationship while a test fiber is wrapped around and between them. The rods further provide structural integrity for the test apparatus while it is being placed in an environmental chamber 27 mounted on the load analyzer. These rods are then released from the sheaves to begin the predetermined tensile load stressing rate.

In the representative configuration the chamber is a cylindrically-shaped shell that can be sealed along its base and filled with a fluid, for example, seawater. Experience has demonstrated that the effects of a fluid such as seawater on a fiber affects the fiber's tensile strength. That is to say, the fluid quickly reacts with molecular imperfections, cracks etc. to compromise the fiber's strength. Immersion in the fluid while being subjected to tensile loads gives valid indications of the fiber's strength under actual operational conditions.

In operation, one-half loop of optical fiber 11 is looped around fixed sheave 16. The ends of the fiber are brought up and about rotatable sheave 12 and stuck onto double-stick tape 24. Several wraps on the tape by both ends of the optical fiber assure that the fiber will not slip but remain in place during a test operation.

The sheaves and fiber are placed into chamber 27 with loop-shaped member 20a being releaseably engaged by hook-shaped member 20b. The securing devices holding rods 25 and 26 onto crossheads 14 and 20 are released slightly after both crossheads are connected to the tensile load analyzer. The crossheads are displaced slightly with respect to one another so that the optical fiber is stretched taut. Because rotatable sheave 12 is journaled, tension on the two lengths of the optical fiber is equalized. Tension is applied from the tensile load analyzer and responsive readouts from the strain gauge are monitored. After fatigue occurs at the breaking stress point, the rods are once again secured to crossheads 14 and 20, members 20a and 20b are disengaged and the whole unit is withdrawn from the environmental chamber and readied for the next test.

Although optical fibers have been satisfactorily tested, any small fiber can be tested with this apparatus. Numerous modifications come to mind. Error is reduced by not creating torsional stresses or pinching stresses during the testing operation.

Obviously, many other modifications and variations of the present invention are possible in the light of the above teachings. It is therefore to be understood that within the scope of the appended claims the invention may be practiced otherwise than as specifically described.

What is claimed is:

1. An apparatus for mounting a fiber to determine its tensile strength by a strain gauge in a plurality of environments comprising:

means for providing a rotatable rounded bearing surface being shaped to receive a fiber and being journaled in a fixed support, the rotatable rounded bearing surface providing means is connected to the strain gauge and has a radius of curvature greatly in excess of the fiber's diameter;

means longitudinally aligned with the rotatable rounded bearing surface providing means for defining a fixed rounded bearing surface, the fixed rounded bearing surface defining means has a radius of curvature greatly in excess of the fiber's diameter; and means disposed on the rotatable rounded bearing surface providing means for adhesively mounting a wrapped length of a fiber to be tested thereon without generating any spurious failure inducing stresses.

2. An apparatus according to claim 1 further including:

means disposed to contain the fiber, the rotatable rounded bearing surface providing means, the fixed rouned bearing surface defining means and the adhesively mounting means for ensuing the immersion thereof in a fluid.

3. An apparatus according to claim 2 in which the rotatable rounded bearing surface providing means and the fixed rounded bearing surface defining means are a pair of sheaves.

4. An apparatus according to claim 3 in which the adhesively mounting means is a strip of double stick tape adhering to one of the sheaves for receiving the wrapped length of fiber thereon.

5. An apparatus according to claim 4 in which the immersion ensuring means is a cylindrical shell.

* * * * *